US006833545B2

(12) United States Patent
Axelsson

(10) Patent No.: US 6,833,545 B2
(45) Date of Patent: Dec. 21, 2004

(54) METHOD AND DEVICE FOR PERFORMING ANALYSES IN PARALLEL

(75) Inventor: Jan Axelsson, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 81 days.

(21) Appl. No.: 10/276,758

(22) PCT Filed: May 30, 2001

(86) PCT No.: PCT/EP01/06167

§ 371 (c)(1),
(2), (4) Date: Mar. 17, 2003

(87) PCT Pub. No.: WO01/93309

PCT Pub. Date: Dec. 6, 2001

(65) Prior Publication Data

US 2003/0155499 A1 Aug. 21, 2003

(30) Foreign Application Priority Data

May 31, 2000 (SE) .............................. 0002066

(51) Int. Cl.$^7$ ............................................... H01J 39/34
(52) U.S. Cl. .................... 250/297; 250/281; 250/282; 250/287; 250/288; 250/290; 250/292; 250/298
(58) Field of Search ............................. 250/281, 282, 250/283, 284, 286, 287, 288, 290, 292, 423, 392, 398, 424, 425, 297, 298

(56) References Cited

U.S. PATENT DOCUMENTS

| | | | | |
|---|---|---|---|---|
| 3,740,551 A | * | 6/1973 | Green ........................ 250/297 |
| 3,868,507 A | | 2/1975 | Panitz |
| 4,524,275 A | * | 6/1985 | Cottrell et al. ............. 250/298 |
| 4,535,236 A | * | 8/1985 | Batey ........................ 250/292 |
| 4,578,589 A | * | 3/1986 | Aitken .................... 250/492.2 |
| 5,008,537 A | * | 4/1991 | Toita et al. ................ 250/309 |
| 5,087,815 A | * | 2/1992 | Schultz et al. ............. 250/309 |
| 5,128,543 A | * | 7/1992 | Reed et al. ................ 250/287 |
| 5,440,124 A | * | 8/1995 | Kelly et al. ................ 250/309 |
| 5,466,932 A | * | 11/1995 | Young et al. .............. 250/289 |
| 5,652,427 A | * | 7/1997 | Whitehouse et al. ....... 250/288 |
| 5,763,880 A | * | 6/1998 | Nisiyama et al. ........... 250/310 |
| 5,808,300 A | | 9/1998 | Caprioli |
| 5,920,068 A | * | 7/1999 | Marsh ........................ 250/309 |
| 6,417,511 B1 | * | 7/2002 | Russ et al. ................. 250/292 |
| 6,469,299 B2 | * | 10/2002 | Chutjian et al. ............ 250/292 |
| 6,528,786 B2 | * | 3/2003 | Marsh ........................ 250/309 |

FOREIGN PATENT DOCUMENTS

| WO | WO87/00682 | 1/1987 |
|---|---|---|
| WO | WO98/40907 | 9/1998 |
| WO | WO99/50667 | 10/1999 |
| WO | WO99/65058 | 12/1999 |

OTHER PUBLICATIONS

Osom, R. "Secondary Ion Mass Spectrometry Imaging", Applied Spectroscopy Reviews, Marcel Dekker, Inc., New York, NY, US, Feb. 1, 1994, pp. 67–116.

Migeon, H., et al. "Ion microscope and ion microprobe analysis under oxygen, cesium and gallium bombardment", International Journal of Mass Spectrometry and Ion Processes, Elsevier Scientific Publishing Co., Amsterdam, NL, vol. 143, May 25, 1995, pp. 51–63.

Savina, M., et al. "Chemical imaging of surfaces with laser desorption mass spectrometry", TRAC, Trends in Analytical Chemistry, Analytical Chemistry, Cambridge, GB, vol. 16, No. 5, May 1, 1997, pp. 242–252.

Rohrbacher, A., et al. "Multiple–ion–beam time–of–flight mass spectrometer", Review of Scientific Instruments, Aug. 2001, AIP, USA, vol. 72, No. 8, pp. 3386–3389.

* cited by examiner

Primary Examiner—John R. Lee
Assistant Examiner—David A. Vanore
(74) Attorney, Agent, or Firm—Royal N. Ronning, Jr.; Yonggang Ji; Stephen G. Ryan

(57) ABSTRACT

The present invention relates to analysis devices having means (3, 5, 7) for producing a plurality of ion beams of samples substantially simultaneously; mass separating means for individually mass separating each ion beam in parallel and detecting means ($13_1$–$13_n$) for detecting said mass separated ion beams substantially simultaneously, and to methods for using such devices.

7 Claims, 1 Drawing Sheet

METHOD AND DEVICE FOR PERFORMING ANALYSES IN PARALLEL

FIELD OF THE INVENTION

The present invention relates to devices and methods of the type mentioned in the preambles of the independent claims for performing analyses substantially in parallel.

PRIOR ART

Mass spectrometers are instruments that produce ions from one or more sample substances, sort these ions based on their mass-to-charge ratios and then record the relative abundance of each species of ion present in a spectrum. These tasks are performed on the samples in sequence. An example of mass spectrometry using "MALDI" (matrix-assisted laser desorption/ionisation) is described in U.S. Pat. No. 5,770,860. In this document it is described how thousands of samples can be loaded as spots onto sample supports which are then introduced into the ion source of a mass spectrometer for analysis. The analysis of each spot takes about 2 seconds.

If a sample such as a piece of tissue is cut into thin sections, then it can be attached to a MALDI sample slide. This sample can be thought of as a grid of points (or pixels, if the points will be used to make an image) to be analysed. For example, it may be desired to analyse a grid of 200×200 pixels (i.e. 40 000 samples). With the prior art methods and devices, it will take 80 000 seconds (over 22 hours) to perform the mass spectrometry analysis. Once the samples have been analysed then data processing of the 40 000 samples also requires a lot of computer memory and processing time. For example, with a spectrum length of 32 000 sample points and a 16-bit intensity scale, more than 2 Gigabytes of memory will be needed to store a single 200×200 pixel picture. Performing data analysis on this picture, e.g. using peak detection algorithms to form an image of where the mass-to-charge ratio is e.g. 889.3, using prior art devices would require a large amount of disc space and hours of analysis time.

SUMMARY OF THE INVENTION

The present invention aims to reduce the time needed to analyse a plurality of samples. According to the present invention, this is achieved by means of a device having the features presented in the characterising part of claim 1 or by means of a method having the features mentioned in the characterising part of independent claim 7.

The invention will now be described in more detail by means of non-limiting examples of embodiments in the following figure and description.

DETAILED DESCRIPTION OF EMBODIMENTS ILLUSTRATING THE INVENTION

Figure 1:
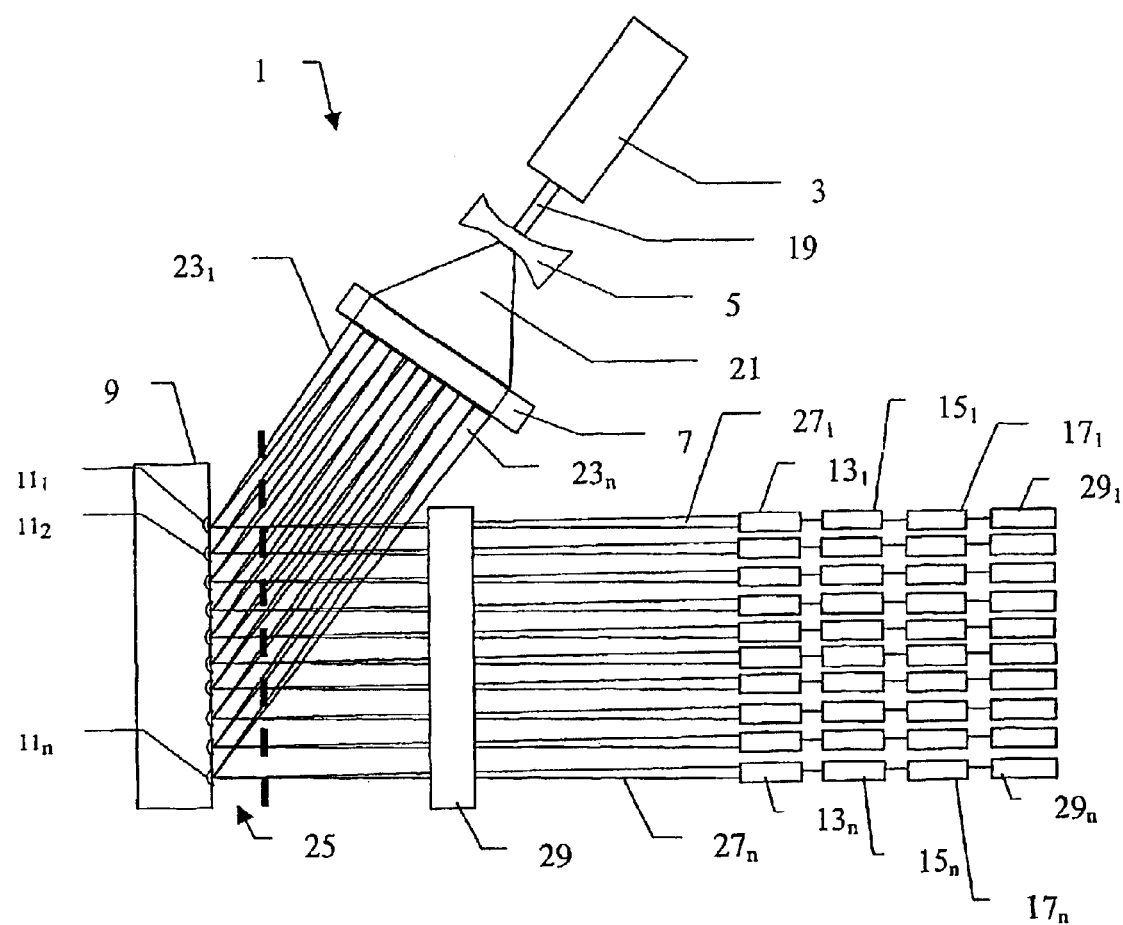
FIG. 1 shows schematically an example of one embodiment of the present invention.

FIG. 1 shows schematically a first embodiment of a MALDI mass spectrometer 1 in accordance with the present invention. In this embodiment n samples can be processed in parallel, where n is any desired number e.g. 10, 100, 200, 400 etc. Mass spectrometer 1 comprises ionising means, such as a laser 5, which can emit pulses of short beams of parallel light 19. These parallel pulses of light 19 are directed towards diverging means, such as a diverging lens 5 that emits diverging pulses 21 of laser light. These pulses 21 are directed towards a converging means, such as an array of n converging lenses 7 that break each pulse up into n narrower converging beams $23_1$–$23_n$. Each of these individual beams $23_1$–$23_n$ is focused onto its own target sample $11_1$–$11_n$ on a MALDI target slide 9. Target samples $11_1$–$11_n$ can be anything which it is desired to sample, for example biological samples from n different sources, e.g. a plate with n different blood samples, or they could be n different regions on a slice of tissue. Thus, beam $23_1$ is focused onto target sample $11_1$ (e.g. blood sample 1 or tissue region 1), beam $23_2$ is focused onto target $11_2$ (e.g. blood sample 2 or tissue region 2), etc. Each of these beams $23_1$–$23_n$ can cause laser desorption of their respective target sample $11_1$–$11_n$. One ion beam $27_1$–$27_n$ can be extracted from each target sample $11_1$–$11_n$ and accelerated in an ion acceleration gap 25 so that there are n ion beams produced substantially simultaneously. These beams are directed, via a focusing means, such as ion-optical system 29, that focuses the ion beams, to n detection means, such as detection surfaces $13_1$–$13_n$, one for each of the n ion beams. Each detection surface $13_1$–$13_n$ is connectable to its own analogue-to-digital (A/D) converter $15_1$–$15_n$, which in turn is connectable to its own individual signal processing means such as digital signal processor $17_1$–$17_n$. Each signal processor $17_1$–$17_n$ can be connected to its own individual data storage mean, such as hard disc $29_1$–$29_n$ for storing the information used by the signal processor $17_1$–$17_n$.

An example of how a mass spectrometer in accordance with the present invention can be used follows. Let us take the case when it is desired to form a 3-dimensional map, with 1 mm between each sampled area, of the peptides in a tissue sample that is in the form of a 1 cm×1 cm×1 cm cube. The tissue sample can be frozen and then sliced into 2000 thin sections, each 50 micrometers thick. Each of these sections can be mounted on an individual MALDI target slide 9 or, alternatively, some or all of the sections can be mounted on the same slide 9. In order to test the composition of the tissue sections at 1-mm intervals it is necessary to take 100 analysis samples per section. These analysis samples preferably are spaced equally over the 1 cm×1 cm×1 mm section and form the target samples $11_1$–$11_{100}$. Each of these target samples can be considered to be a pixel in the final image that will represent the composition of the tissue sample. The slide 9 can be mounted in a device in accordance with the present invention, in which the device has a 10×10 array of converging lens 7, which makes the incoming laser beam up into 100 beams $23_1$–$23_{100}$, each directed to a respective target sample/pixel $11_1$–$11_{100}$ on the section (alternatively on one of the sections) on the target slide 9. If an OBB GL-3300 laser is used then the power available for laser desorption is 1.45 mJ. If the threshold energy for laser desorption is about 15 mJ/cm² then this laser can perform laser desorption on a total spot size of about 0.1 cm²=10 mm². Using this laser to produce one hundred simultaneous laser beams $23_1$–$23_{100}$ means that each beam can have a spot size of about 0.1 mm². This gives a maximum pixel spot size of about 0.3×0.3 mm. In order to account for expected losses in the system, it is prudent to have smaller pixel sizes, for example 0.2×0.2 mm. Typically MALDI imaging requires about 10 laser pulses per sample and with a typical laser repetition rate of 10 Hz it takes 1 second to ionise a spot. In the present invention the laser pulses are fired through the optical system 5, 7 so that one hundred samples $11_1$–$11_{100}$ are ionised simultaneously. This produces one hundred ion beams $25_1$–$25_{100}$ that can be accelerated in the ion acceleration gap 25. This means that 100 target samples are ionised in parallel instead of sequentially, which means that the time to mass separate 100 samples is reduced by a factor of 100.

Each of these ion beams $25_1$–$25_{100}$ can be detected by an individual detection surface $13_1$–$13_{100}$ and the time taken for ions to reach the detector (the time of flight) recorded. The detected information from each detector surface $13_1$–$13_{100}$ can be converted into digital form by an individual A/D converter $15_1$–$15_{100}$. This digitised information from each individual A/D converter can be processed by its own individual signal processor $17_1$–$17_{100}$ which can have its own individual hard disc $29_1$–$29_n$. As 100 hard disks are used to store the information from the 100 samples, then for each image these hard disks each individually only have to store one hundredth of the information that the prior art hard disk needs to hold. If each hard disks is of the order of 10 Gbytes then 1 Tbyte of data can be stored for rapid access in these 100 hard disks. This could, for example, be 500 images, each having 200×200 pixels. These 100 hard disks can be accessed simultaneously by the 100 signal processors, which means that the processing time can be reduced by a factor of 100. The signal processors can be utilised in the further processing of data and form a parallel computer.

The invention is not limited to producing and processing 100 samples at the same time but can easily be reduced or expanded to process any desired number of samples in parallel.

While the present invention has been illustrated by an example where one laser is used to produce a plurality of laser beams, it is also conceivable to use a plurality of lasers to produce a plurality of beams simultaneously. These beams could be focused onto different samples in order to increase the number of samples ionised at the same time without having to use more powerful lasers. It is also conceivable to use a plurality of lasers to produce a plurality of beams in sequence. If two lasers are focused on the same samples and fire pulses in turn then it will be possible to halve the time need to generate each image. Using three or more lasers would further decrease the time needed to generate an image.

Additionally, if some loss of performance is acceptable then it is also conceivable to allow two or more analogue-to-digital converters to share the same digital signal processor in order to reduce the number of digital signal processors required. Similarly, allowing two or more digital signal processors to share the same hard disc can reduce the number of hard discs.

Performance may be improved by connecting each analogue-to-digital converter to two or more digital signal processors and switching the output over from one digital signal processors to another.

Furthermore, the invention is not limited to MALDI mass spectrometry but is also applicable to liquid chromatography mass spectrometry (LC-MS), in which case the samples to be ionised could be provided simultaneously from a number of electrospray needles and detected in parallel by a plurality of detectors.

Alternatively a plurality of electrospray needles (e.g. 100 electrospray needles) could be each supplied with a sample which is ionised, preferably substantially continuously, from the needle, and the ions from each individual needle could be collected in one of a plurality of ion traps (e.g. 100 ion traps). Each ion trap could have an output leading to a single detector and switching means could be arranged to allow each ion trap in turn to output ions to the single detector. In this way a plurality of sample may be ionised in parallel and their compositions detected sequentially. The use of ion traps permits most of the ionised sample to be detected. Detection times could be halved by using 2 detectors. However these embodiments of the present invention require the use of a plurality of ion traps. If the sample material is sufficiently abundant such that it would only be necessary to detect a small proportion of the sample, then it is conceivable to forego the use of ion traps and just direct each ion stream in turn to the detector. Thus with 100 electrospray needles the stream of ions from each needle would be directed to the detector for about 1 percent of the time e.g. for 1 hundredth of a second every 1 second. As no ion traps are used, this device would be cheaper than a device using ion traps although a proportion, in this example 99%, of each sample would not be detected. Although this means that the samples are not detected in parallel, the time between each sample is so short that they can be considered to be detected substantially simultaneously.

The present invention is not limited to use with mass spectrometry but is also adaptable to any other analysis method, especially those producing ions from the samples being analysed.

Additionally, the present invention is not limited to parallel devices using analogue-to-digital converting but is equally applicable to devices using time-to-digital converting. In this method a signal level threshold is set and events have a signal strength above this threshold are defined to be ions while any signal below this threshold is defined to be noise. High gain detectors are used to count each event above the threshold and the time when the event occurred is recorded. This gives a better sensitivity than A/D converting as each individual ion can be counted. It is conceivable to provide device with both analogue-to-digital converting means and time-to-digital converting means and a control means for switching between the two converting means. The control means, such as a computer, could be programmed to switch to time-to-digital converting at a high gain when few hits are detected, and to switch to analogue-to-digital converting with a lower gain when more hits are detected.

While the invention has been illustrated by an embodiment in which the mass separating takes place in a time of flight mass spectrometer, it is of course conceivable to use any other mass separating means using radio-frequency quadrupoles, ion-cyclotron resonance, ion trap, magnetic sectors, etc.

What is claimed is:

1. A mass spectrometer for analysing a plurality of spatially separated target samples from a sample comprising a means (3, 5, 7) for ionising a plurality of said target samples ($11_1$–$11_n$) in parallel in order to produce a plurality of spatially separated ion beams ($27_1$–$27_n$) substantially simultaneously, said means including at least one laser; and a plurality of separate detection means ($13_1$–$13_n$) arranged to each detect substantially simultaneously said plurality of ion beams ($27_1$–$27_n$) wherein each of said detectors detects only one of said ion beams and produces a signal relating to the constituents of the ion beam ($27_1$–$27_n$) detected by it.

2. The mass spectrometer of claim 1 further comprising an A/D converter means ($15_1$–$15_n$) for analogue-to-digital converting said separate signals in parallel.

3. The mass spectrometer of claim 1, further comprising a means for time-to-digital converting said separate signals in parallel.

4. The mass spectrometer of claim 1, further comprising an A/D converter means ($15_1$–$15_n$) for analogue-to-digital converting said separate signals in parallel, means for time-to-digital converting said separate signals in parallel and a control means for switching between analogue-to-digital converting and time-to-digital converting said separate signals, and vice versa.

5. The mass spectrometer of claim 1, further comprising a signal processing means (17$_1$–17$_n$) for signal processing said separate signals in parallel.

6. A method for analysing target samples from a sample by mass spectrometry comprising the steps of:

producing a plurality of spatially separate ion beams from said target samples substantially simultaneously;

separately detecting the constituents of said separate ion beams substantially simultaneously: and analogue-to-digital converting signals related to the constituents of said ion beams substantially simultaneously.

7. A method for analysing target samples from a sample by mass spectrometry comprising the steps of:

producing a plurality of spatially separate ion beams from said target samples substantially simultaneously;

separately detecting the constituents of said separate ion beams substantially simultaneously; and time-to-digital converting signals related to the constituents of said ion beams substantially simultaneously.

\* \* \* \* \*